(12) United States Patent
Takahashi et al.

(10) Patent No.: US 8,101,935 B2
(45) Date of Patent: Jan. 24, 2012

(54) INSPECTION APPARATUS AND INSPECTION METHOD

(75) Inventors: Kazuo Takahashi, Naka-gun (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 418 days.

(21) Appl. No.: 12/272,211

(22) Filed: Nov. 17, 2008

(65) Prior Publication Data

US 2009/0140180 A1  Jun. 4, 2009

(30) Foreign Application Priority Data

Nov. 30, 2007 (JP) ................................ 2007-311342

(51) Int. Cl.
*G01N 21/88* (2006.01)
(52) U.S. Cl. ........... 250/559.4; 250/559.41; 250/559.45; 250/221; 356/237.3
(58) Field of Classification Search ................... 250/221, 250/222.1, 548, 559.4, 559.41–559.45; 356/237.1, 356/237.3, 237.4; 382/149; 375/350
See application file for complete search history.

(56) References Cited

U.S. PATENT DOCUMENTS
4,603,703 A * 8/1986 McGill et al. ................. 600/544

FOREIGN PATENT DOCUMENTS
JP  63-143830  6/1988
JP  6-249791  9/1994
* cited by examiner

*Primary Examiner* — Kevin Pyo
(74) *Attorney, Agent, or Firm* — McDermott Will & Emery LLP

(57) ABSTRACT

Reflected light caused by the state of the surface of a wafer, a foreign material or a defect is superimposed on a haze frequency component caused by the type and thickness of a film or a surface irregularity. It has therefore been difficult to accurately measure the haze frequency component by use of a fixed threshold value. In order to detect a haze frequency component caused by a haze present on the surface of an object to be inspected, light propagating from the object to be inspected is detected and converted into an electric signal. The electric signal is sampled at a predetermined sampling time interval and converted into digital data. A frequency component caused by a foreign material, a defect or the like is separated from the digital data to ensure that a haze frequency component is selected. The haze frequency component is caused by a stain attached to the surface of the wafer, hazy tarnish, a surface irregularity or the like.

11 Claims, 6 Drawing Sheets

INSPECTION APPARATUS AND INSPECTION METHOD

BACKGROUND OF THE INVENTION

1. Field of the Invention

The present invention relates to an apparatus and method for inspection of the surface of an object to be inspected.

2. Description of the Related Art

Conventionally, as described in JP-A-63-143830, since various defects are present on a silicon wafer plate (that is a semiconductor material) and cause a reduction in the quality of an integrated circuit manufactured, the silicon wafer plate is inspected by a plate defect inspection apparatus.

Recently, since the density of an integrated circuit has been increased, and rigorous inspection has been carried out on defects, it is necessary that the types of defects be discriminated and detected.

Many types of defects may be present on a wafer plate. One type of the defects is a haze such as a stain attached to the surface of the plate, hazy tarnish, or a surface irregularity. It is requested to detect those defects.

The haze is distributed in a relatively large area and has an extremely thin film shape. A conventional defect detection method is to detect light that is generated from a fine particle (such as dust) or a microscopic scratch and scattered in an extremely small area. It is difficult that this method is used to detect a haze. Therefore, an effective method for detecting such a haze is required.

SUMMARY OF THE INVENTION

A signal generated from an object to be detected includes a high frequency fluctuation component caused by a defect or a foreign material present on the surface of a wafer plate, aside from a haze such as a stain attached to the surface of the plate, hazy tarnish, or a surface irregularity.

The high frequency fluctuation component is determined based on parameters which are the spot size of illumination light, the speed of a unit which moves an object to be detected, and the position of the object after the movement of the object. Therefore, the high frequency fluctuation component is not constant.

In a conventional technique, the high frequency fluctuation component is removed or suppressed by an analog filter. However, since setting of a cut-off frequency is specified based on a circuit constant, it is difficult to flexibly change the high frequency fluctuation component. Thus, the high frequency fluctuation component cannot be determined based on the abovementioned conditions.

In consideration of distortion of a passing signal, it is necessary that the passing signal have a sufficient frequency band. It is therefore difficult to set an attenuating frequency band to be sufficiently large. The high frequency fluctuation component cannot be removed or suppressed with high accuracy.

Since the fluctuating frequency component cannot be removed, a threshold value for detecting and determining a haze frequency component needs to be increased. However, the sensitivity of the detection is degraded due to the increase in the threshold value.

An object of the present invention is to reduce a high frequency component. Another object of the present invention is to reduce a component caused by a defect (foreign material) present on the surface of a wafer plate and to accurately detect and determine a haze frequency component without an increase in a threshold value for the detection determination.

An inspection apparatus according to the present invention includes: an illumination unit which illuminates the surface of an object that is to be inspected and placed on a movable stage; and an optical detection unit which detects light reflected by the surface of the object and converts the detected light into an electric signal, wherein a frequency component caused by a defect or a foreign material is separated from data of the electric signal, and a frequency component (hereinafter referred to as a haze frequency component) caused by a haze such as a stain attached to the surface of the object, hazy tarnish, a surface irregularity, or the like is selected.

According to the present invention, the haze frequency component can be selected. In addition, the present invention provides an inspection apparatus and an inspection method that are capable of reducing a frequency component caused by a defect or a foreign material present on the surface of an object to be inspected, and detecting and determining a haze frequency component caused by a stain, hazy tarnish, a surface irregularity or the like in a stable manner.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Figure 1A:
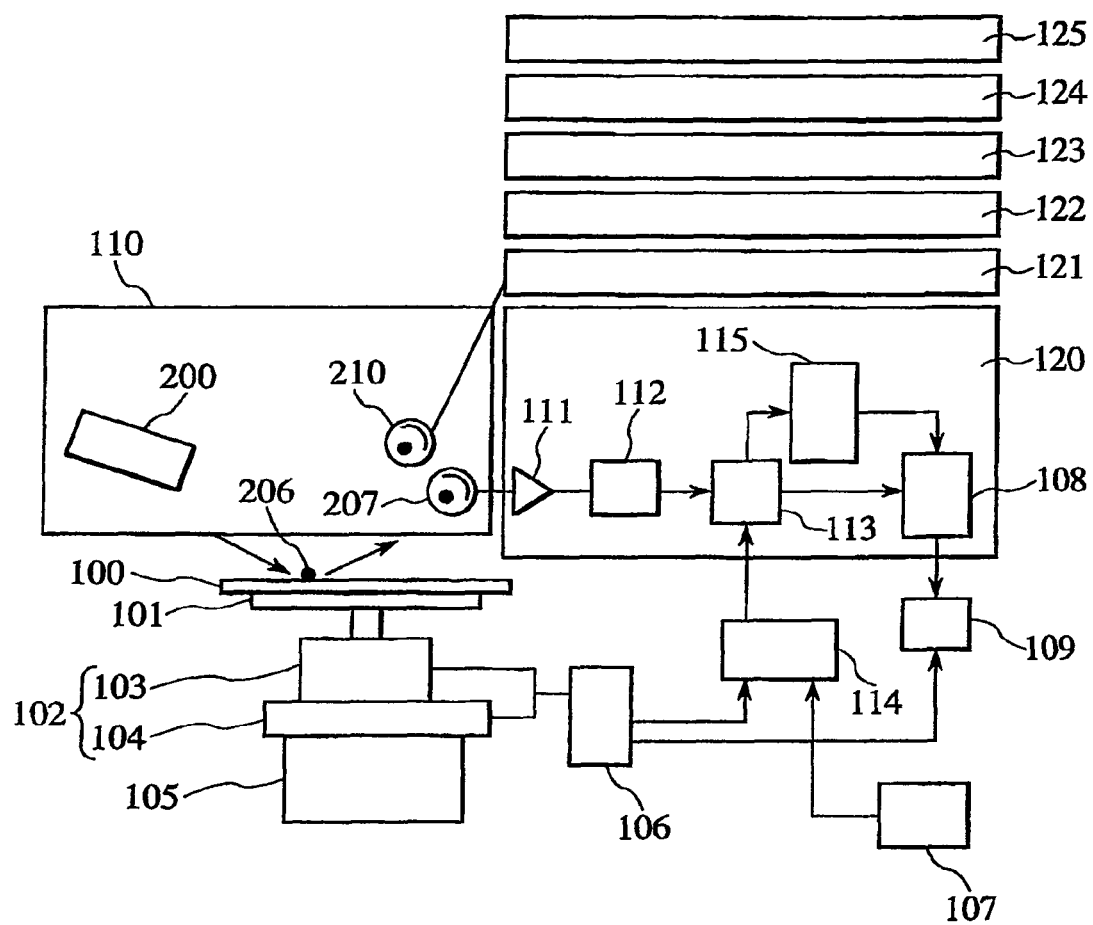
FIGS. 1A and 1B are diagrams showing the outline configuration of an inspection apparatus according to an embodiment of the present invention.
Figure 1B:
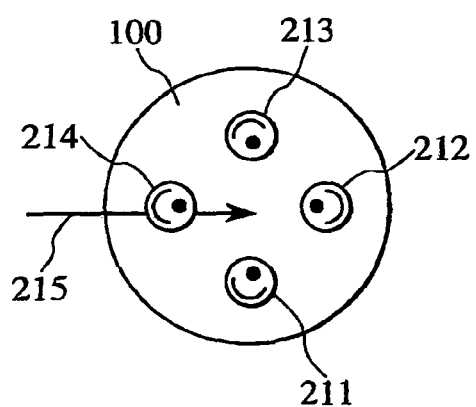

FIG. 1A is a diagram showing a defect (foreign material) inspection apparatus using a method for detecting a defect or a foreign material according to an embodiment of the present invention. FIG. 1B is a plan view of a semiconductor wafer 100.

The semiconductor wafer 100 (that is an object to be inspected) is vacuum sucked by a chuck 101. The chuck 101 is placed on a movable stage 102 for moving the object to be inspected. The stage 102 is constituted by a rotation stage 103 and a translational stage 104. The stage 102 is placed on a Z stage 105. The rotation stage 103 performs a rotational motion θ, while the translational stage 104 performs a translational motion r.

Figure 2A:
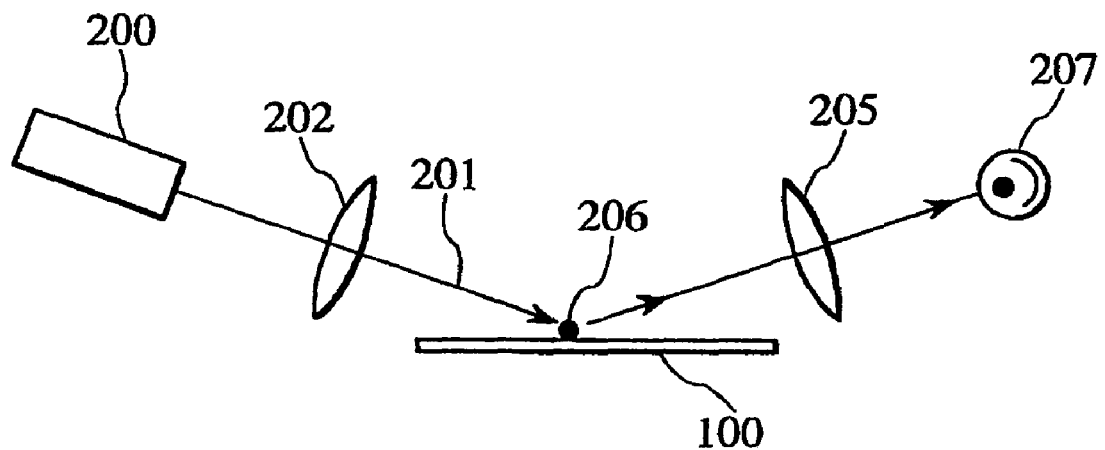
FIGS. 2A and 2B are diagrams showing an illumination spot according to the embodiment of the present invention.
Figure 2B:
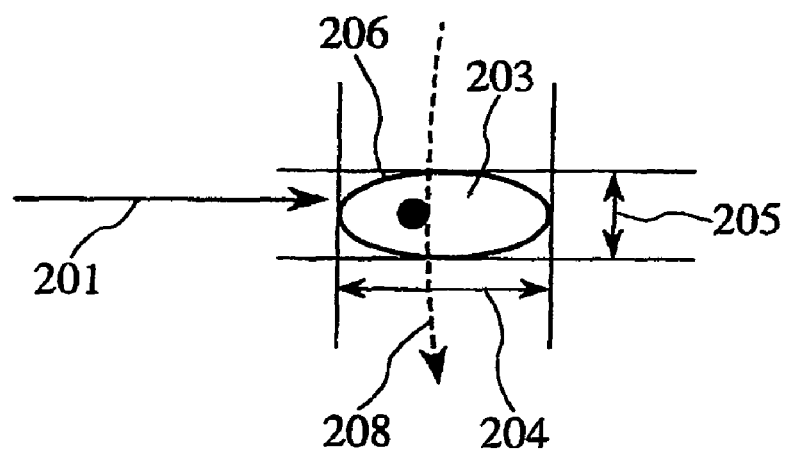

FIG. 2A shows an illumination detection optical system arranged above the semiconductor wafer 100. FIG. 2B is a plan view of the semiconductor wafer 100.

An illumination light source 200 uses a laser light source. The illumination light source 200 emits a beam 201. The beam 201 is incident on a lens 202. Then, an illumination spot 203 having a predetermined size is formed on the surface of the semiconductor wafer 100. Light, with which the semiconductor wafer 100 is illuminated, is P-polarized, for example. The illumination light is incident on the surface of the semiconductor wafer 100 at the Brewster's angle (inclined with respect to a normal to the surface of the semiconductor wafer 100) for crystal silicon or at an angle substantially equal to the Brewster's angle. Thus, the illumination spot 203 has a substantially elliptical shape. The inside of an area in which the intensity of the illumination light is reduced to $1/e^2$ (e is the base of natural logarithm) of the intensity of the illumination light at a central part of the illumination spot 203 is defined as the illumination spot 203.

The width of the illumination spot 203 in the direction of a longitudinal axis of the illumination spot 203 is indicated by reference numeral 204. The width 204 is represented by d1. The width of the illumination spot 203 in the direction of a short axis of the illumination spot 203 is indicated by reference numeral 205. The width 205 is represented by d2. The illumination spot 203 is subjected to scanning 208 performed with the rotational motion θ.

Figure 3:
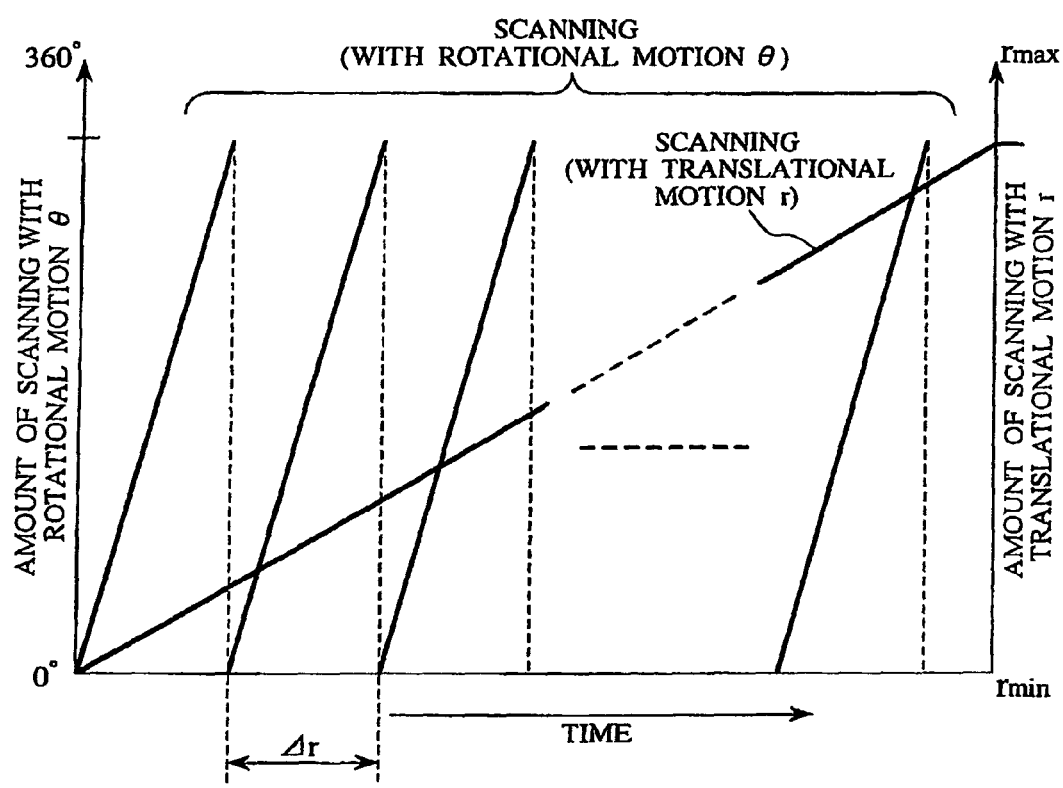
FIG. 3 is a graph showing scanning according to the embodiment of the present invention.

As shown in FIG. 3, the movable stage 102 (for moving the object to be inspected) combines the rotational motion θ with the translational motion r and adjusts the combined motion with elapsed time and thereby causes the illumination spot 203 to be relatively spirally scanned on the substantially entire surface of the semiconductor wafer 100. While the rotation stage 103 rotates 360 degrees, the position of a scanned area is changed by a distance Δr. When the distance Δr is larger than the width d1, the semiconductor wafer 100 is not irradiated with the illumination light in the spiral scanning. In this case, an area that is not inspected is present. Therefore, the distance Δr is typically set to be smaller than the width d1. In the present embodiment, the illumination spot 203 is scanned from an inner circumference of the semiconductor wafer 100 to an outer circumference of the semiconductor wafer 100. The illumination spot 203 may be scanned from the outer circumference to the inner circumference.

In the present embodiment, the rotation stage 103 is driven at a substantially constant angular speed, and the translational stage 104 is driven at a substantially constant linear speed, in the substantially entire area (ranging from the inner circumference to the outer circumference) of the semiconductor wafer 100.

Figure 4A:
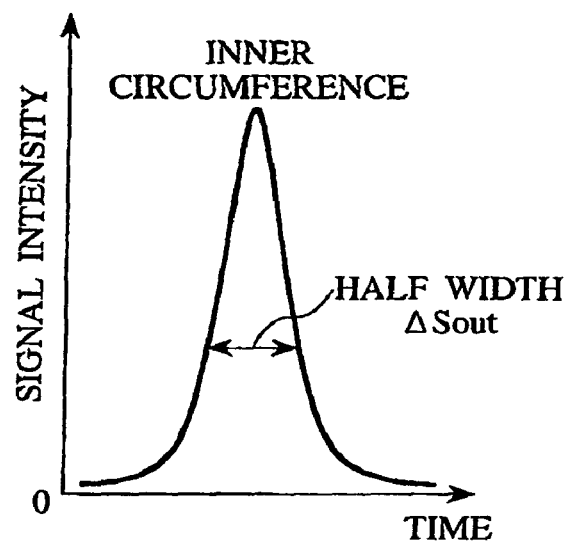
FIGS. 4A to 4C are graphs showing a difference (of half widths of signals) generated due to a difference between the positions of scanned defects (or scanned foreign materials) according to the embodiment of the present invention.
Figure 4B:
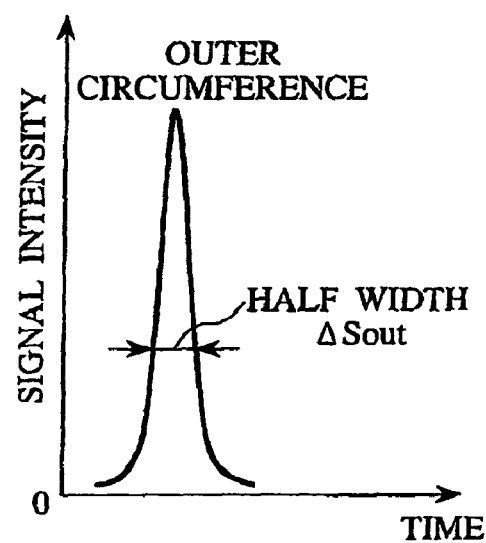
Figure 4C:
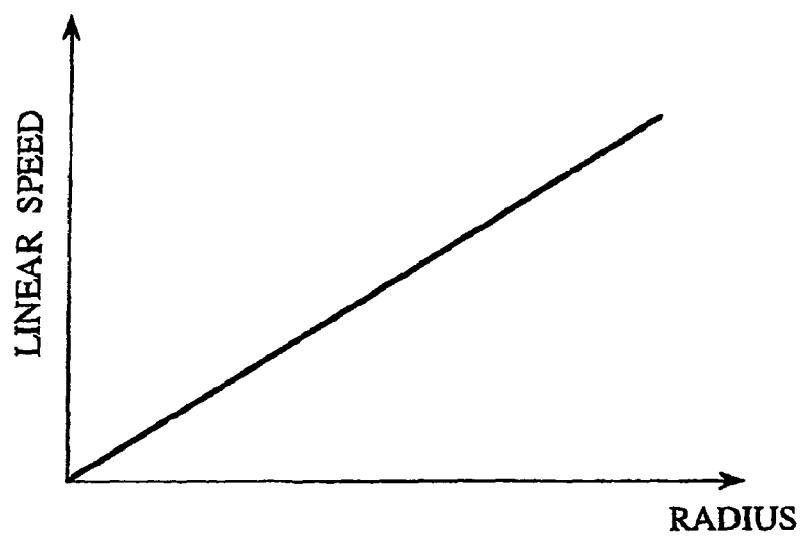

FIG. 4C is a graph showing that a relative moving linear speed of the illumination spot 203 to the surface of the semiconductor wafer 100 is increased as the position of the illumination spot 203 is changed from the inner circumference to the outer circumference. FIG. 4A shows a signal intensity obtained when the inner circumference is illuminated, while FIG. 4B shows a signal intensity obtained when the outer circumference is illuminated.

The movable stage 102 for moving the object to be inspected has an inspection coordinate detection mechanism 106 attached thereto. The inspection coordinate detection mechanism 106 is adapted to detect a main scanning coordinate position θ and a sub scanning coordinate position r. In the present embodiment, an optical read rotary encoder is used to detect the main scanning coordinate position θ, and an optical read linear encoder is used to detect the sub scanning coordinate position r. Each of the encoders may be replaced with a sensor having another detection principle as long as the sensor is capable of detecting a rotational angle of the rotation stage 103 or the position of the translational stage 104 on a straight line with high accuracy.

A condenser lens 205 is configured to be capable of collecting light scattered from a microscopic foreign material according to Rayleigh scattering at a small elevation angle to efficiently capture the scattered light. In this configuration, a foreign material 206 passes the illumination spot 203, and an optical detector 207 acquires a signal (scattered light signal) of the scattered light. In the present embodiment, a photomultiplier is used as the optical detector 207. The photomultiplier may be replaced with an optical detector having another detection principle as long as the optical detector is capable of detecting light scattered from a foreign material with high sensitivity.

As described above, the rotation stage 103 is driven at a substantially constant angular speed in the substantially entire area (ranging from the inner circumference to the outer circumference) of the semiconductor wafer 100 in the present embodiment. A relative moving linear speed of the illumination spot 203 to the surface of the semiconductor wafer 100 is increased as the position of the illumination spot 203 is changed from the inner circumference of the semiconductor wafer 100 to the outer circumference of the semiconductor wafer 100.

Therefore, a time for which a foreign material present on the outer circumference of the semiconductor wafer 100 crosses the width 205 (distance d2) of the semiconductor wafer 100 in the direction of the short axis of the illumination spot 203 is shorter than a time for which a foreign material on the present on the inner circumference of the semiconductor wafer 100 crosses the width 205 (distance d2) of the semiconductor wafer 100 in the direction of the short axis. A time variable wave form of the scattered light signal acquired from the optical detector 207 through an amplifier 111 is generally shown in FIG. 4B. In FIG. 4B, the half width of the signal peak is reduced as the foreign material is located more closely to the outer circumference (i.e., as the foreign material is located on a larger diameter of the spiral of the scanned area).

Next, signal processing according to the present embodiment is described below.

As shown in FIG. 1, the amplifier 111 receives the scattered light signal from the optical detector 207 and amplifies the scattered light signal. After that, an analog-to-digital (A/D) converter 112 samples the scattered light signal at a predetermined sampling time interval ΔT and converts the scattered light signal into digital data. The sampling time interval ΔT is determined to ensure that the signal waveforms shown in FIGS. 4A and 4B can be sampled with a sufficient time resolution.

When the half width obtained when the outermost circumference is illuminated, which is the minimum signal waveform width in FIGS. 4A and 4B, is ΔSout, ΔT=ΔSout÷10. This sampling makes it possible to obtain a time-series digital data group corresponding to the signal waveforms shown in FIGS. 4A and 4B.

The sampling time interval is variable in consideration of a tradeoff between improvement of the sampling accuracy and the amount of data to be processed.

Figure 5:
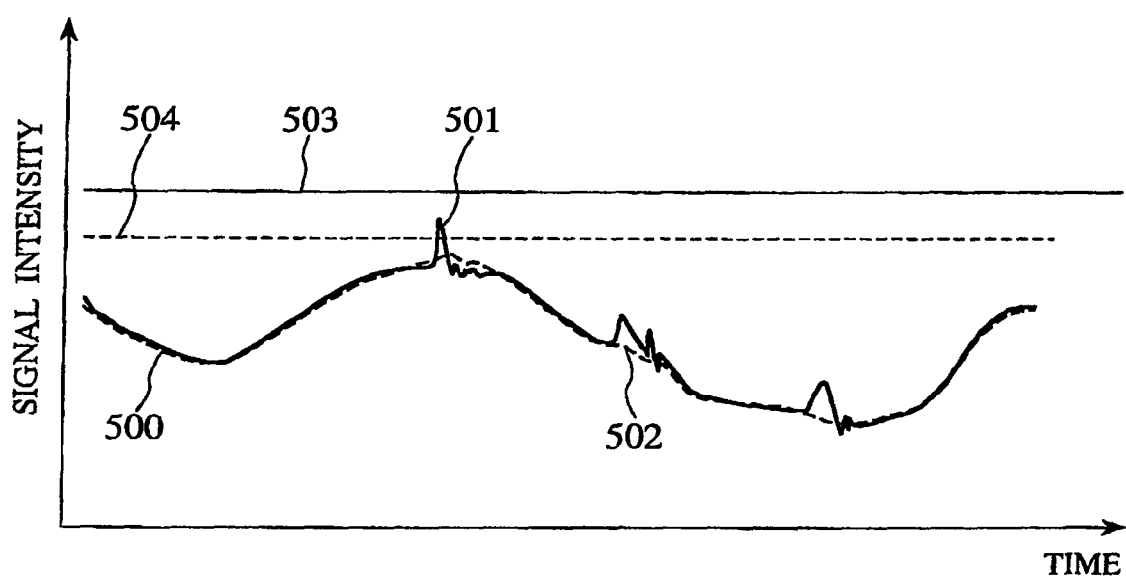
FIG. 5 is a graph showing a signal caused by a defect or foreign material and a threshold value according to the embodiment of the present invention.

The time-series digital data group includes a low frequency signal component (that is fundamentally necessary and is a haze component) 500 shown in FIG. 5 and defect signal component 501 caused by a defect or a foreign material.

The haze frequency component is caused by a haze such as a stain attached to the surface of the object to be inspected, hazy tarnish, a surface irregularity, or the like. The high frequency component of the defect signal is caused by a fine particle, a microscopic scratch or the like present on the surface of the semiconductor wafer.

The component 501 including the defect signal (depending on the size of the defect or the foreign material) varies based on the rotational speed of the movable stage 102 (for moving the object to be inspected) for main scanning, the coordinate position (obtained from the inspection coordinate detection mechanism 106) of a scanned area, the size of the illumination spot, the type and thickness of a film formed on the surface of the object to be inspected, the surface irregularity, crystal orientation, and the amount of warpage. The defect signal component 501 is not constant. In order to accurately calculate the haze frequency component, it is necessary to remove a frequency component caused by a foreign material or a defect.

In the present embodiment, a variable low pass filter 113 performs processing on the digital data obtained from the A/D converter 112 to remove the high frequency component caused by the foreign material or the defect and obtain information on only the intensity of scattered light corresponding to the haze frequency component.

A cut-off frequency of the variable low pass filter 113 is controlled by an arithmetic unit 114 based on the rotational speed of the movable stage 102 (for moving the object to be inspected), the coordinate position (obtained from the inspection coordinate detection mechanism 106) of the scanned area, the size of the illumination spot, the type and thickness of the film formed on the surface of the object to be inspected, the surface irregularity, the crystal orientation, and the amount of the warpage. A calculation parameter of the arithmetic unit 114 is based on information obtained from the inspection coordinate detection mechanism 106 and from a higher-level CPU 107.

The cut-off frequency is represented by the following expression: the cut-off frequency=1÷((the minor axis of the illumination spot)÷(the rotational speed)÷(2×(the circular constant)×(the radial coordinate position)))÷A. The symbol A is specified based on the type and thickness of the film formed on the surface of the object to be inspected, the surface irregularity, the crystal orientation, and the amount of the warpage. The type and thickness of the film formed on the surface of the object to be inspected, the surface irregularity, the crystal orientation, and the amount of the warpage are set by a user and calculated in the apparatus.

The intensity (obtained as a result of the abovementioned data processing) of the scattered light is compared with a predetermined detection threshold value by a haze determination mechanism 108. When the intensity of the scattered light is higher than the threshold value, the haze determination mechanism 108 generates haze determination information. When the haze determination mechanism 108 generates the haze determination information, a haze coordinate detection mechanism 109 calculates the coordinate position of the detected haze based on the information obtained from the inspection coordinate detection mechanism 106.

In the present embodiment, the variable low pass filter 113 performs the processing on the signal obtained from the amplifier 111 to remove an effect of the high frequency component caused by the defect or the foreign material. Then, haze determination is performed.

As a result, when the component 501 has the high frequency component (of the defect signal obtained from the defect or the foreign material) superimposed thereon as shown in FIG. 5, the high frequency component is removed. The defect signal component 501 becomes a component 502 (indicated by a dotted line shown in FIG. 5). It is therefore not necessary to set the threshold value to a conventional threshold value 503 for the high frequency component of the defect signal. In the present embodiment, the threshold value is set to a threshold value 504 to ensure that the haze frequency component can be appropriately detected.

The haze determination is to compare a measured value with a value calculated based on optical characteristics and physical characteristics of the wafer and make a determination based on the comparison. In order to maintain a margin (to avoid a false detection) between a theoretical value and an actual value, it has been necessary that a determination value have a margin.

When an input parameter for the calculation is lost due to an additional unexpected condition for a process for manufacturing a wafer, a value calculated based on the comparison is false. This causes a false detection and prevents the detection.

To prevent the above case, when a haze frequency component is discriminated in detail, haze value data indicating a pre-specified normal haze value is registered in a reference memory 115. Measured data on the haze frequency component caused by the haze located at the coordinate position is compared with data on a frequency component caused by a normal object located at the same coordinate position.

This reference is variable per scanning of one circle of the wafer and per specified area.

This method reduces the margin (to avoid a false detection) between the theoretical value and the actual value and avoids false setting of the value calculated based on the comparison. Also, the method makes it possible to accurately detect the haze frequency component.

The haze frequency component may have a characteristic in a specific direction of the reflected light depending on its compositional factor. A light receiving mechanism for receiving reflected light from all directions has a small directional characteristic. It has been difficult that the light receiving mechanism detects a haze frequency component.

To avoid the above problem, an optical detector 210 is arranged on an imaginary line forming an elevation angle (with respect to the surface of the semiconductor wafer 100) different from the elevation angle formed between the surface of the semiconductor wafer 100 and the propagation direction (of the beam 201) in which the optical detector 207 is arranged. Optical detectors 211 to 214 are arranged at a certain offset angular interval with respect to an incident direction 215 of the laser beam. An offset angle for the elevation angle and an offset angle for the laser beam incident angle are set to ensure that a haze frequency component is characterized for each reflection direction. The reflected light includes light scattered due to the irradiation of the object to be inspected, light interfering due to the irradiation of the object to be inspected, and light diffracted due to the irradiation of the object to be inspected.

The amplifier 111, the A/D converter 112, the variable low pass filter 113, the reference memory 115, and the haze determination mechanism 108 are included in a detection data processing unit 120. Detection data processing units 121, 122, 123, 124, and 125 are respectively provided for the optical detectors 210 to 214. The detection data processing units 121 to 125 perform parallel processing. In this configuration of the apparatus, a haze frequency component having a characteristic in a specific direction can be accurately detected.

Figure 6:
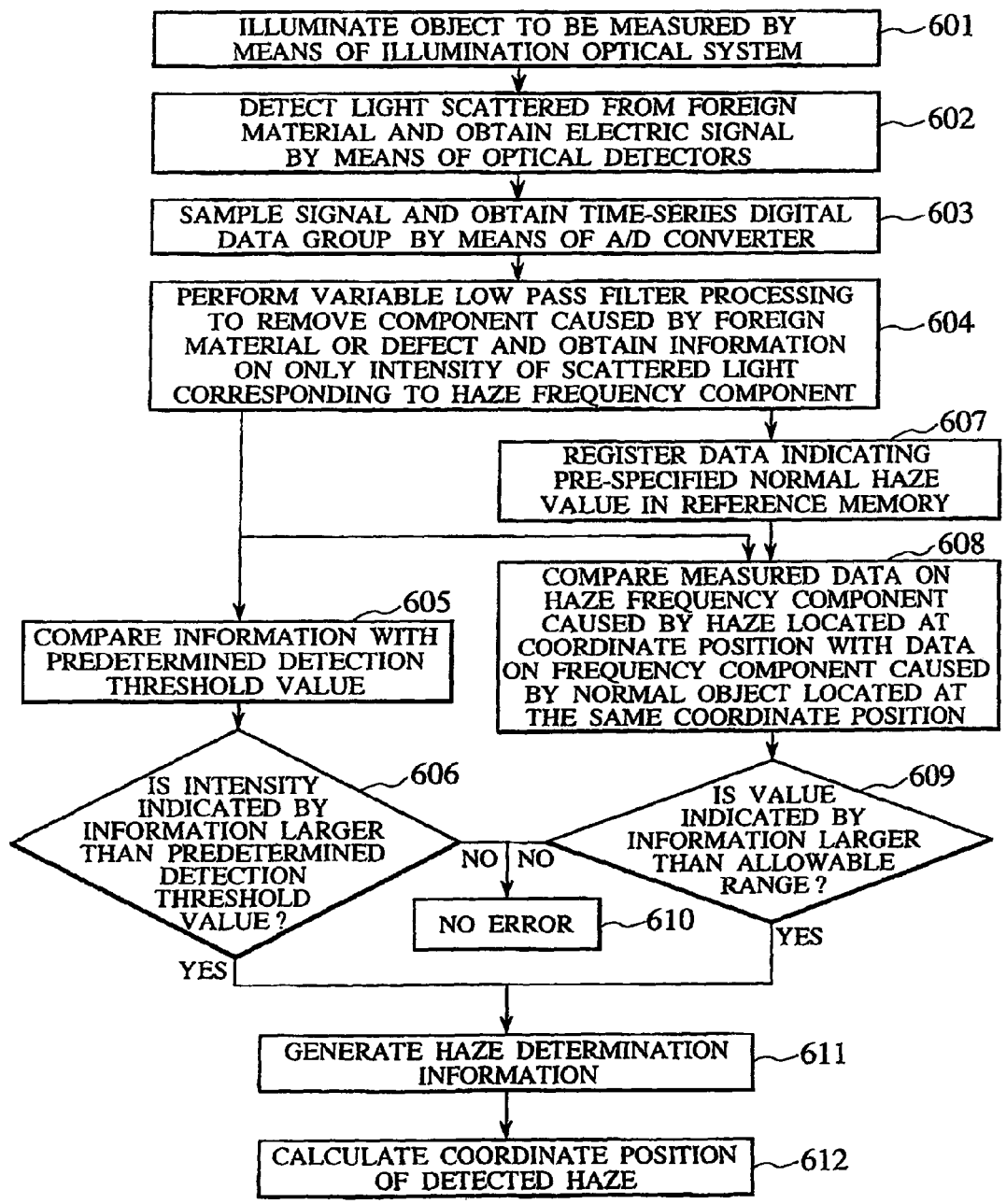
FIG. 6 is a flowchart showing an inspection according to the embodiment of the present invention.

Next, FIG. 6 is a flowchart showing the inspection described above.

An illumination/detection optical system 110 (illumination unit) illuminates the object to be inspected in step 601. An optical detection unit includes the optical detectors 207, 210, 211 to 214. The optical detection unit detects scattered light including a frequency component (caused by a defect, a foreign material and the like) and a haze frequency component (caused by a haze such as a stain attached to the surface of the semiconductor wafer, hazy tarnish, and a surface irregularity) and obtains an electric signal in step 602.

The electric signal is amplified by the amplifier 111. The A/D converter 112 samples the amplified signal to obtain a time-series digital data group in step 603. The variable low pass filter 113 performs variable low pass filter processing on the time-series digital data group to ensure that: a frequency component caused by a defect, a foreign material or the like is separated and removed from the time-series digital data group; a haze frequency component (caused by a haze such as a stain attached to the surface of the semiconductor wafer, hazy tarnish, and a surface irregularity) is selected; and information on only the intensity of scattered light corresponding to the haze frequency component is obtained, in step 604.

The information on only the intensity of the scattered light corresponding to the haze frequency component is compared with a predetermined detection threshold value in step 605. When the intensity indicated by the information is larger than the predetermined detection threshold value in step 606, the haze determination mechanism 108 generates haze determination information in step 611. Then, the haze coordinate detection mechanism 109 calculates the coordinate position of the detected haze in step 612.

After step 604, the data indicating the pre-specified normal haze value is registered in the reference memory 115 in step 607. In step 608, the data indicating the pre-specified normal haze value is compared with the information (obtained in step 604) on only the intensity of the scattered light corresponding to the haze frequency component. In the comparison, measured data on the haze frequency component caused by the haze located at the coordinate position is compared with data on a frequency component caused by a normal object located at the same coordinate position.

When the intensity indicated by the information is larger than an allowable range in the comparison in step 608 (in step 609), the haze determination mechanism 108 generates haze determination information in step 611. Then, the haze coordinate detection mechanism 109 calculates the coordinate position of the detected haze in step 612.

When the intensity indicated by the information is not larger than the allowable range in step 609, it is determined that there is no error in step 610. When the intensity indicated by the information is not larger than the detection threshold value in step 606, it is also determined that there is no error in step 610.

When the intensity indicated by the information is not larger than the allowable range in step 609 and not larger than the detection threshold value in step 606, it may be determined that there is no error.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An inspection apparatus comprising:
    an illumination unit which illuminates the surface of an object that is to be inspected and placed on a movable stage;
    an optical detection unit which detects light propagating from the surface of the object and converts the detected light into an electric signal;
    an A/D converter which converts the electric signal to digital data; and
    a processing unit which separates and removes a first frequency component from the digital data and selects a haze frequency component caused by a haze,
    wherein, in order to determine normality of the haze frequency component, data on the haze frequency component caused by the haze located at a coordinate position is compared with data on a frequency component caused by a normal object located at the same coordinate position.

2. The inspection apparatus according to claim 1, wherein the light includes at least one type of light reflected by the surface of the object and light scattered from the surface of the object,
    the first frequency component caused by a defect in the form of a microscopic scratch or a foreign material has a higher frequency than that of the haze frequency component caused by a haze in the form of a stain attached to the surface of the object, hazy tarnish or a surface irregularity.

3. The inspection apparatus according to claim 1, wherein the processing unit has a digital filter processing function.

4. The inspection apparatus according to claim 3, wherein the digital filter processing function includes a frequency band limit filter processing function for removing the first frequency component.

5. The inspection apparatus according to claim 4, wherein the processing unit selects the haze frequency component based on data information including at least one of: a rotational speed of the movable stage for main scanning; the coordinate position of the movable stage, which is obtained by a coordinate detection unit; and the size of an illumination spot formed by the illumination performed by the illumination unit, and has a function capable of changing a combination of the data information in accordance with a change in the data information.

6. The inspection apparatus according to claim 4, wherein the processing unit has a function for using data information including at least one of: the type and thickness of a film formed on the surface of the object to be inspected; a surface irregularity; crystal orientation; and the amount of warpage, to select the haze frequency component and limit the digital data to the haze frequency component.

7. An inspection method which illuminates with light an object that is to be inspected and placed on a movable stage to inspect a region present on the surface of the object or inspect the inside of the object that is located near the surface of the object, comprising the steps of:
    detecting light propagating from the object to be inspected and converting the detected light into an electric signal;
    sampling the electric signal at a predetermined sampling time interval and converting the sampled electric signal into digital data; and
    separating from the digital data a frequency component caused by a foreign material or a defect and selecting a haze frequency component caused by a haze in the form of a stain attached to the surface of the object, hazy tarnish or a surface irregularity,
    wherein, in order to determine normality of the haze frequency component, data on the haze frequency component caused by the haze located at a coordinate position is compared with data on a frequency component caused by a normal object located at the same coordinate position.

8. The inspection method according to claim 7, wherein the step of separating the frequency component from the digital data and selecting the haze frequency component is performed within a time for which the object to be inspected passes an illumination spot formed by the illumination with the inspection light.

9. The inspection method according to claim 7, wherein the step of separating the frequency component from the digital data and selecting the haze frequency component is digital filter processing, which is frequency band limit filter processing which removes the frequency component obtained from the foreign material or defect.

10. The inspection method according to claim 7, wherein in the step of separating the frequency component from the digital data and selecting the haze frequency component, the haze frequency component is selected based on data information including at least one of: a rotational speed of the movable stage for main scanning; the coordinate position of the movable stage, which is obtained by a coordinate detection unit; and the size of an illumination spot formed by the illumination performed by the illumination unit, to ensure that the digital data is limited to the haze frequency component, and a combination of the data information can be changed in accordance with a change in the data information.

11. The inspection method according to claim 9, wherein in the defect detection processing, data information including at least one of: the type and thickness of a film formed on the surface of the object to be inspected; a surface irregularity; crystal orientation; and the amount of warpage, is used to determine a limitation method of limiting the frequency band limit filter processing.

\* \* \* \* \*